(12) United States Patent
Hashimoto et al.

(10) Patent No.: US 8,487,986 B2
(45) Date of Patent: Jul. 16, 2013

(54) IMPEDANCE MATCHING APPARATUS AND ENDOSCOPE INCLUDING THE SAME

(75) Inventors: Hidenori Hashimoto, Hachioji (JP); Yasuhiro Tanaka, Machida (JP); Hideaki Ishihara, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/456,472

(22) Filed: Apr. 26, 2012

(65) Prior Publication Data

US 2012/0274752 A1    Nov. 1, 2012

Related U.S. Application Data

(63) Continuation of application No. PCT/JP2011/067965, filed on Aug. 5, 2011.

(30) Foreign Application Priority Data

Aug. 9, 2010   (JP) ................................. 2010-178834

(51) Int. Cl.
  *H04N 5/378* (2011.01)
  *H03H 7/40* (2006.01)
(52) U.S. Cl.
  USPC .............................................. 348/65; 348/76
(58) Field of Classification Search
  None
  See application file for complete search history.

(56) References Cited

U.S. PATENT DOCUMENTS

| | | | | |
|---|---|---|---|---|
| 5,031,036 | A * | 7/1991 | Kikuchi et al. | 348/71 |
| 7,917,209 | B2 * | 3/2011 | Joo et al. | 607/6 |
| 2002/0171733 | A1 * | 11/2002 | Takami et al. | 348/76 |
| 2009/0027490 | A1 * | 1/2009 | Hirai et al. | 348/65 |
| 2010/0060725 | A1 * | 3/2010 | Jung et al. | 348/65 |
| 2010/0134606 | A1 * | 6/2010 | Avni et al. | 348/65 |

FOREIGN PATENT DOCUMENTS

| | | |
|---|---|---|
| JP | 06-105807 | 4/1994 |
| JP | 2001-016141 | 1/2001 |
| JP | 2003-204929 | 7/2003 |
| JP | 2005-229292 | 8/2005 |
| JP | 2006-055223 | 3/2006 |
| JP | 2009-045366 | 3/2009 |

* cited by examiner

*Primary Examiner* — Gims S Philippe
*Assistant Examiner* — Reza Aghevli
(74) *Attorney, Agent, or Firm* — Scully, Scott, Murphy & Presser, P.C.

(57) ABSTRACT

An impedance matching apparatus includes: a cable that transmits a rectangular wave outputted from a solid image pickup device; a correlated double sampling circuit that performs scanning of the rectangular wave by sampling the rectangular wave with a timing of a signal clamp pulse being changed, based on a timing of the feed-through sampling pulse fixed at a timing at which the rectangular wave by the cable indicates a high value; a variable resistance provided at a tail end side of the cable; and a resistance value varying unit that, that performs the scanning with a resistance value of the variable resistance being changed, based on a signal outputted from the correlated double sampling circuit, changes a resistance value of the variable resistance so as to match a characteristic impedance of the cable.

4 Claims, 14 Drawing Sheets

1A IMPEDANCE MATCHING APPARATUS

IMPEDANCE MATCHING APPARATUS AND ENDOSCOPE INCLUDING THE SAME

CROSS REFERENCE TO RELATED APPLICATION

This application is a continuation application of PCT/JP2011/067965 filed on Aug. 5, 2011 and claims benefit of Japanese Application No. 2010-178834 filed in Japan on Aug. 9, 2010, the entire contents of which are incorporated herein by this reference.

BACKGROUND OF THE INVENTION

1. Field of the Invention

The present invention relates to an impedance matching apparatus and an endoscope including the same, and more particularly, to an impedance matching apparatus that achieves impedance matching in a channel when image pickup signals outputted from an image pickup device at an endoscope distal end portion are transmitted through a cable to a processor, and an endoscope including the impedance matching apparatus.

2. Description of the Related Art

Conventionally, a cable composing a channel from an image pickup device at an endoscope distal end portion to a processor has a length of about a few meters, so that impedance matching of the cable is important in view of a waveform grade. In recent years, a band of output signals from image pickup devices has become wide, and importance of impedance matching has further increased with it. However, cables have considerable impedance variations due to manufactural reasons, and waveform degradation caused thereby is a problem.

Conventional impedance matching methods will be described with reference to FIG. 18 through FIG. 20.

FIG. 18 schematically illustrates a channel of an endoscope. The endoscope includes an insertion portion to be inserted into a body cavity, an operation portion (not shown) connected to a proximal end side of the insertion portion, and a universal cable portion. The insertion portion of the endoscope has a distal end portion including a CCD as a solid image pickup device, a bending portion provided at a proximal end side of the distal end portion, and a flexible pipe portion having flexibility and being provided at a proximal end side of the bending portion. In the insertion portion, a signal cable, through which the CCD transmits and receives image pickup signals and power supply voltage, is inserted. The signal cable is additionally connected to a processor, not shown, via the operation portion and the universal cable portion.

In FIG. 18, reference numeral 10 denotes an endoscope distal end portion, reference numeral 20 denotes a cable having characteristic impedance ZO, and reference numeral 30 denotes a part of an analog front end portion.

The distal end portion 10 includes a CCD 11, a base resistance R1, an NPN transistor Q1 composing an emitter-follower, and an emitter resistance R2 as an output resistance. Collectors of the CCD 11 and the transistor Q1 are supplied with power supply voltage Vdd from outside.

The analog front end portion 30 includes a direct current termination resistance R3, a direct current cutting capacitor C1, an alternating current termination resistance R4, a preamplifier 32, and the like. The alternating current termination resistance R4 is composed of a variable resistance such as a trimming resistor that can be manually adjusted.

A condition of impedance matching is as follows: (an output resistance value of the transistor Q1)+(a resistance value of the resistance R2)=ZO=(a resistance value of the resistance R4).

Since variations in characteristic impedance ZO of the cable 20 can be smoothed by changing a value of the alternating current termination resistance R4, if a CCD output waveform is observed in transmission through the channel in FIG. 18 with the resistance R4 as a variable resistance that can be manually adjusted, a waveform as shown in FIG. 19 or FIG. 20 can be seen. A CCD output waveform can be seen by observing an outputted waveform from the analog front end portion 30 using a waveform observing apparatus.

FIG. 19 is a CCD output waveform with impedance matching obtained, and FIG. 20 is a CCD output waveform with impedance matching not being obtained. In FIG. 19, reference character f1 denotes a feedthrough part, f2 denotes a signal part, and f0 denotes a resetting portion. If impedance matching is not obtained, since a waveform in which reflected waves are superimposed on CCD output as shown in FIG. 20 is provided, such a waveform with impedance matching achieved as shown in FIG. 19 can be obtained by changing a value of the resistance R4 while a waveform of the CCD output is being observed.

Conventional arts related to a cable length of an endoscope are disclosed in, for example, Japanese Patent Application Laid-Open Publication Nos. 6-105807, 2006-055223, and 2001-016141.

Japanese Patent Application Laid-Open Publication No. 6-105807 discloses a signal processing apparatus of an electronic endoscope apparatus in which even if an electronic endoscope having a different length is used, without converting an operation timing, a correlated double sampling circuit and the like are effectively operated as well as a circuit configuration is simplified, which facilitates handling.

Japanese Patent Application Laid-Open Publication No. 2006-055223 discloses an endoscope whose signal connector includes a connector substrate on which a signal pattern for transmitting an output signal from a CCD apart from a drive circuit is provided in order to prevent a drive signal from mixing as a noise. Thereby, influence of noise owing to a drive signal can be reduced and even if a type of a solid image pickup device is different, it is easy to apply the endoscope thereto.

Japanese Patent Application Laid-Open Publication No. 2001-016141 discloses a cable length compensating apparatus for compensating an influence on signal resolution owing to a length of a signal cable used if a video imaging system such as an X-ray video imaging system is set up, the compensation being achieved by the cable compensating apparatus being installable in a signal path along a cable and compensating a signal for the influence of the cable to provide a desired gain across a desired range of a signal frequency.

SUMMARY OF THE INVENTION

An impedance matching apparatus according to an aspect of the present invention includes: a solid image pickup device; driving means that drives the solid image pickup device so that the solid image pickup device outputs a rectangular wave; a cable that transmits the rectangular wave outputted from the solid image pickup device; a correlated double sampling circuit that performs correlated double sampling by fixing a timing of a feedthrough sampling pulse to a timing at which the rectangular wave transmitted by the cable indicates a high value, and with the fixed timing of the feedthrough sampling pulse as a basis, sampling the rectangular wave with a timing of a signal clamp pulse being changed to scan the rectangular wave; a variable resistance provided at a tail end side of the cable and having a variable resistance value; and resistance value varying means that, as a result of the scanning with a resistance value of the variable resistance being changed, based on a signal outputted from the correlated double sampling circuit, changes a resistance value of the variable resistance so that a resistance value of the variable resistance matches a characteristic impedance of the cable.

An endoscope according to an aspect of the present invention is an endoscope including an impedance matching apparatus according to the aspect, further including compensating means that compensates a length of the cable so that the cable length substantially becomes a predetermined length.

DETAILED DESCRIPTION OF THE PREFERRED EMBODIMENTS

Embodiments of the present invention will be described in detail below with reference to the drawings.

[First Embodiment]

Figure 1:
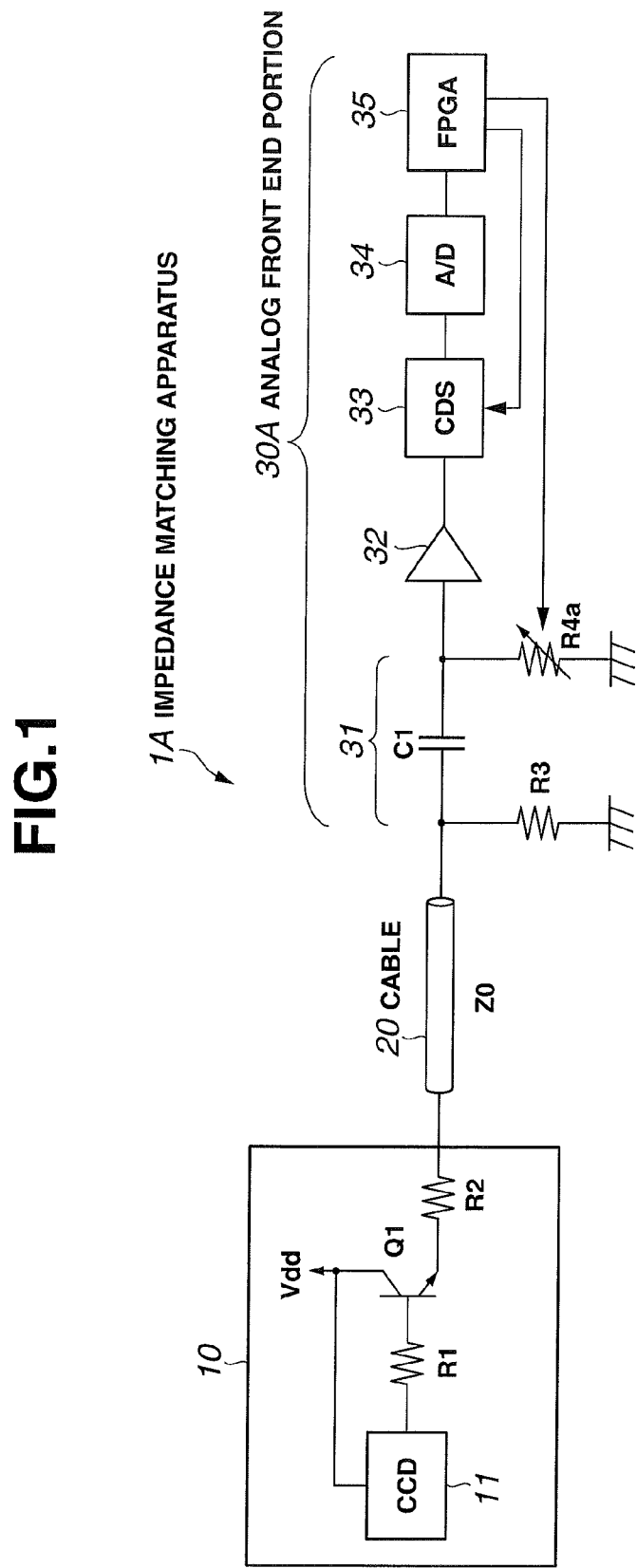
FIG. 1 is a block diagram of an impedance matching apparatus according to a first embodiment of the present invention.

FIG. 1 illustrates a configuration of an impedance matching apparatus according to a first embodiment of the present invention. The present embodiment describes an example in which an impedance matching apparatus 1A is applied to an endoscope 1.

In FIG. 1, the impedance matching apparatus 1A includes a distal end portion 10 having a CCD 11 as a solid image pickup device, a cable 20 as a channel through which CCD 11 output from the distal end portion 10 is transmitted, and an analog front end portion 30A. The analog front end portion 30A can receive the transmitted CCD 11 output (as input), detect a degree of an impedance match or mismatch using sampling by a CDS circuit 33, and generate a control signal depending on the degree to achieve matching of a resistance value of a variable resistance R4a for matching. The cable 20 has characteristic impedance ZO.

The distal end portion 10 includes the CCD 11 as a solid image pickup device, a transistor Q1 composing an emitter-follower, a resistance R1 for leading the CCD 11 output to a base of the transistor Q1, and a resistance R2 for outputting emitter output from the transistor Q1 to the cable 20. Collectors of the CCD 11 and the transistor Q1 in the distal end portion 10 are supplied with power supply voltage Vdd from a direct current power supply in a processor, not shown.

The cable 20 transmits image pickup signals from the CCD 11 to a side of the analog front end portion 30A, and also transmits drive signals for CCD from a drive signal generating circuit, not shown, in the analog front end portion 30A to a side of the CCD 11 through a drive signal line, not shown, in the cable 20.

The analog front end portion 30A includes a termination circuit portion 31, a preamplifier 32, the CDS circuit 33, an A/D converter 34, and an FPGA (an abbreviation for Field Programmable Gate Array) 35 as a control signal generator that can generate a control signal depending on a degree of an impedance match or mismatch using sampling by the CDS circuit 33 to achieve matching of a resistance value of the variable resistance R4a for matching. The FPGA 35 can generate feedthrough sampling pulses (SHP) and signal clamp pulses (SHD) and supply the pulses to the CDS circuit 33, thereby controlling sampling performed by the CDS circuit 33.

The termination circuit portion 31 includes a direct current termination resistance R3, a direct current cutting capacitor C1, and the alternating current termination resistance R4a. The alternating current termination resistance R4a is composed of a variable resistance such as a digital trimming resistor, a resistance value of which can be adjusted with a control signal from the FPGA 35.

As a device for impedance matching control and image processing, an FPGA has been used, but a DSP (digital signal processor) or a CPU (central processing unit) may also be used instead.

In impedance matching, operation functions of the foregoing respective portions in the impedance matching apparatus 1A are as follows.

Drive means, not shown, in the analog front end portion 30A can drive the CCD 11 so that the CCD 11 outputs a rectangular wave.

The cable 20 transmits the rectangular wave outputted from the CCD 11.

The CDS circuit 33 performs correlated double sampling in the following manner: the CDS circuit 33 fixes timing of feedthrough sampling pulses (SHP) to timing indicating a high value of the rectangular wave ('High' part) transmitted through the cable 20, and scans the rectangular wave by sampling the rectangular wave while changing timing of the signal clamp pulses (SHD) with the timing of the fixed feedthrough sampling pulse as a basis. The CDS circuit 33 sequentially samples and holds a level of each of a feedthrough part f1 and a signal part f2, and outputs potential differences of them as signal values.

The alternating current termination resistance R4a as a variable resistance is provided at a termination side of the cable 20 and has a variable resistance value.

The FPGA 35 as resistance value varying means changes a resistance value of the alternating current termination resistance R4a so as to match to a characteristic impedance ZO of the cable 20 based on signals outputted from the CDS circuit 33 as a result of scanning while changing a resistance value of the alternating current termination resistance R4a, which is a variable resistance. More specifically, the FPGA 35 differentiates twice a signal outputted from the CDS circuit 33, and determines a resistance value of the alternating current termination resistance R4a to a resistance value at which an absolute value of a result obtained by the differentiation is a value closest to 0, as a resistance value matching the characteristic impedance of the cable 20.

Figure 2:
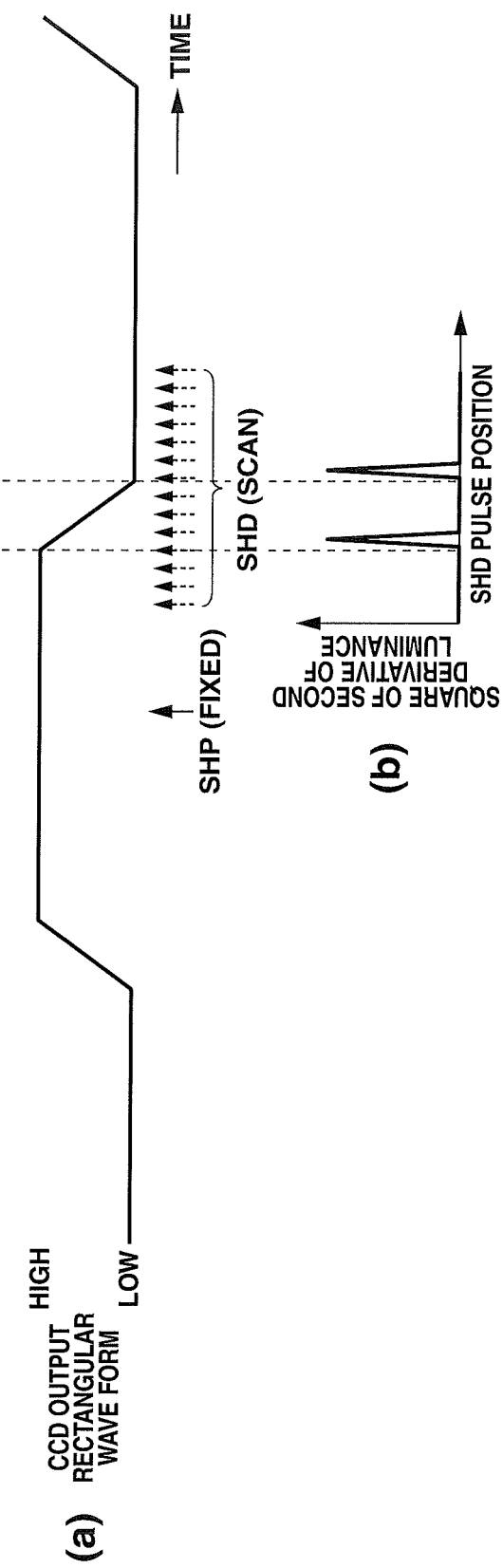
FIG. 2 is an explanation diagram of an impedance matching detecting method with SHD scanning at the time of impedance being matched, in accordance with the first embodiment.
Figure 3:
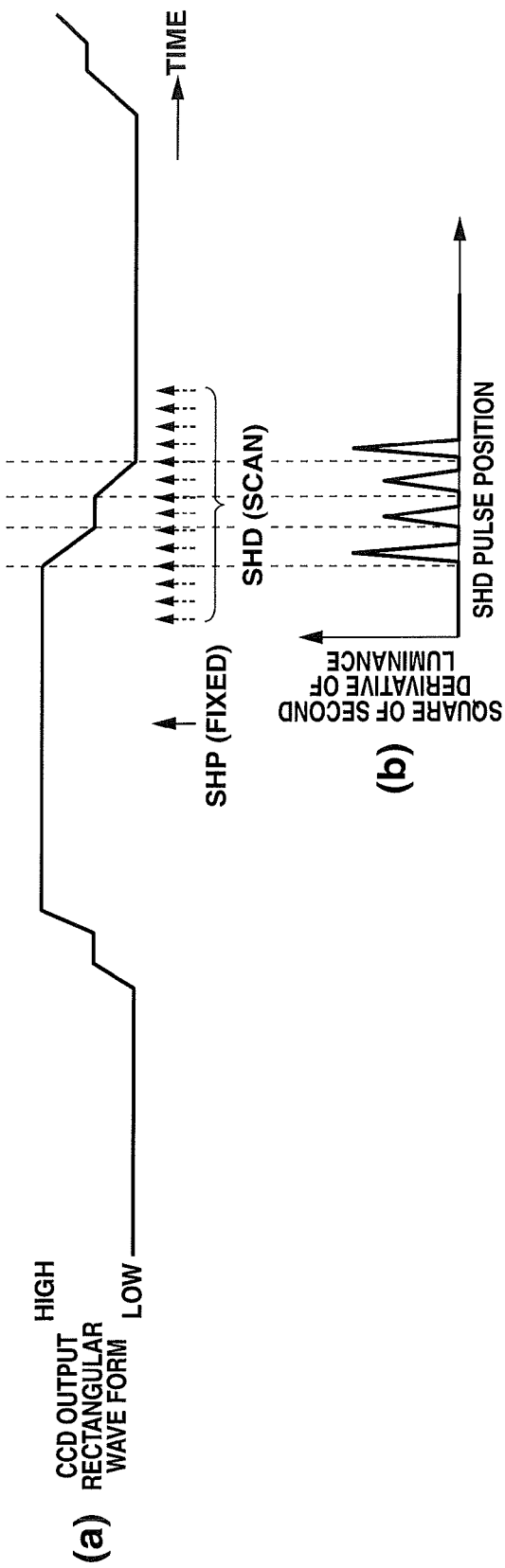
FIG. 3 is an explanation diagram of the impedance matching detecting method with SHD scanning at the time of impedance being mismatched, in accordance with the first embodiment.

Next, an operational effect of FIG. 1 will be described with reference to FIG. 2 to FIG. 4.

Since a condition of impedance matching is "(output resistance of the transistor Q1)+(the resistance R2)=ZO=R4a," variations in the characteristic impedance ZO can be reduced by changing the resistance R4a. The resistance R4a is composed of a digital trimming resistor, a resistance value of which is variable by a value of an electrical control signal. If only resetting of CCD driving is driven, a rectangular wave is outputted from the CCD 11.

As compared with a CCD rectangular output waveform as shown in FIG. 2(a) in which impedance matching is obtained, a CCD rectangular output waveform as shown in FIG. 3(a) in which impedance matching is not obtained is irregularly shaped. Thus, if the CDS circuit 33 sequentially changes (hereinafter, referred to as scans) a timing of a signal clamp pulse (SHD) with feedthrough clamp pulses (SHP) fixed to a high level (HIGH) part of the inputted waveform, a signal depending on a voltage difference is outputted at a changing point of a rectangular wave.

If impedance matching in the channel for CCD output is achieved, as shown in FIG. 2(a), since a CCD output waveform evenly increases from a changing point, brightness (luminance) also evenly changes at the time of a timing scan with signal clamp pulses (SHD). However, if impedance matching is not achieved, since a reflected wave is included, as shown in FIG. 3(a), luminance does not evenly change. It can be determined that matching is more achieved as a second derivative of a luminance value in a signal clamp pulses timing of luminance is closer to 0. Thus, a best termination resistance value R4a can be determined by calculating an absolute value of the second derivative while a termination resistance value R4a is being changed. Instead of calculating an absolute value of a second derivative, a square value of a second derivative value may also be calculated. In the present embodiment, the FPGA 35 calculates a second derivative and feeds it back to the variable resistance R4a, which is a digital trimming resistor.

In fact, FIG. 2(b) and FIG. 3(b) show graphs in which a horizontal axis indicates temporal positions of SHD pulse, and a vertical axis indicates square values of second derivatives of luminance. An appropriate threshold is set for square values of second derivatives and the number of peaks of square values of second derivatives within a certain time period in SHD scanning is detected, and thereby a degree of impedance matching or mismatching can be determined. As shown in FIG. 2(b), if square values of second derivatives within a certain time period in SHD pulse scanning have two peaks, there are two changing points in rises or falls of a luminance waveform, and it can be determined that impedance matching is achieved (Z is equal to R4a). Also, as shown in FIG. 3(b), if square values of second derivatives within a certain time period in SHD pulse scanning have three or more peaks (in the figure, four), there are four or more changing points in rises or falls of a luminance waveform, and it can be determined that impedance matching is not achieved (Z is not equal to R4a).

Figure 4:
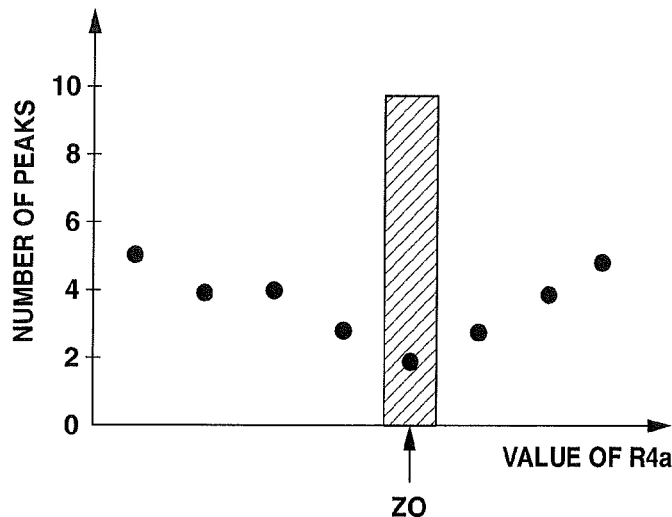
FIG. 4 is an explanation diagram of a method for determining a final matching point from the impedance matching detecting method with SHD scanning in accordance with the first embodiment.

FIG. 4 shows a method for determining a final matching point in an impedance matching detecting method using such SHD scanning. If a horizontal axis indicates values of resistance R4a and a vertical axis indicates the number of peaks of square values of second derivatives in the SHD pulse scanning, it can be seen that the number of peaks reaches a minimum number (two) at a matching point where R4a is equal to ZO, and the numbers of peaks are three or more at the other mismatch points. That is, it can be determined that if the number of peaks is two, a value of R4a is equal to ZO.

Figure 5:
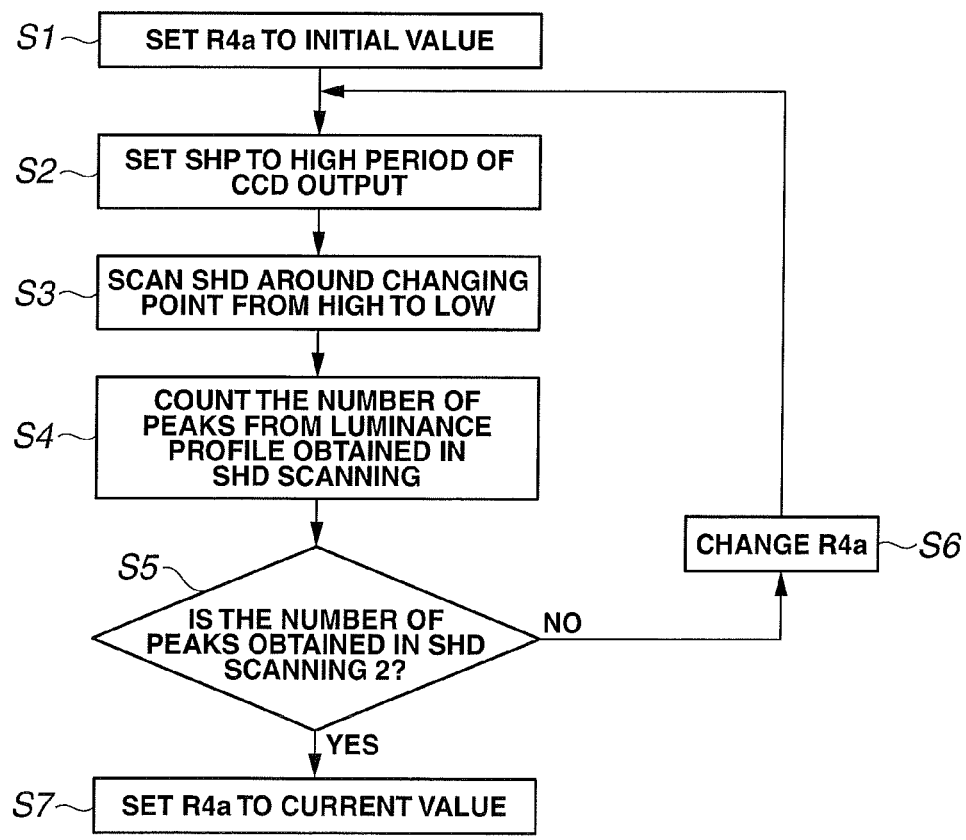
FIG. 5 is a flow chart explaining an operation of the impedance matching apparatus according to the first embodiment.

FIG. 5 explains an operation of the impedance matching apparatus 1A of the first embodiment. The operation of the impedance matching apparatus 1A is controlled by the FPGA 35.

As shown in FIG. 5, first in step S1, the variable resistance R4a is set to an initial value. Then, in step S2, feedthrough sampling pulses SHP are set to a high level (HIGH) period of output from the CCD 11. In step S3, a scan is performed for a certain period around a changing point from the high level (HIGH) to a low level (LOW) in the CCD 11 output while timing of signal clamp pulses SHD are sequentially being changed.

Next, in step S4, the number of peaks is counted from a luminance profile (e.g., square values of second derivatives of CCD output signals) in the SHD scanning Then, in step S5, the FPGA 35 determines whether or not the number of peaks obtained in the SHD scanning is two.

If the number of peaks is not two in step S5, then the resistance R4a is changed, and the FPGA 35 returns to step S2 to repeat steps S2 to S5. If the number of peaks is two in step S5, then the resistance R4a is set to a current value since the impedance matching is achieved.

In this manner, since a termination resistance value can be automatically adjusted to smooth individual differences (variations) in characteristic impedance of cables, degradation of a CCD output signal observed after cable transmission can be reduced to increase a grade of a signal waveform. Moreover, advantageously, it is not necessary to add a cable, a device, or the like for adjusting impedance, so that there is no possibility of increasing the sizes of a cable and a substrate.

Figure 6:
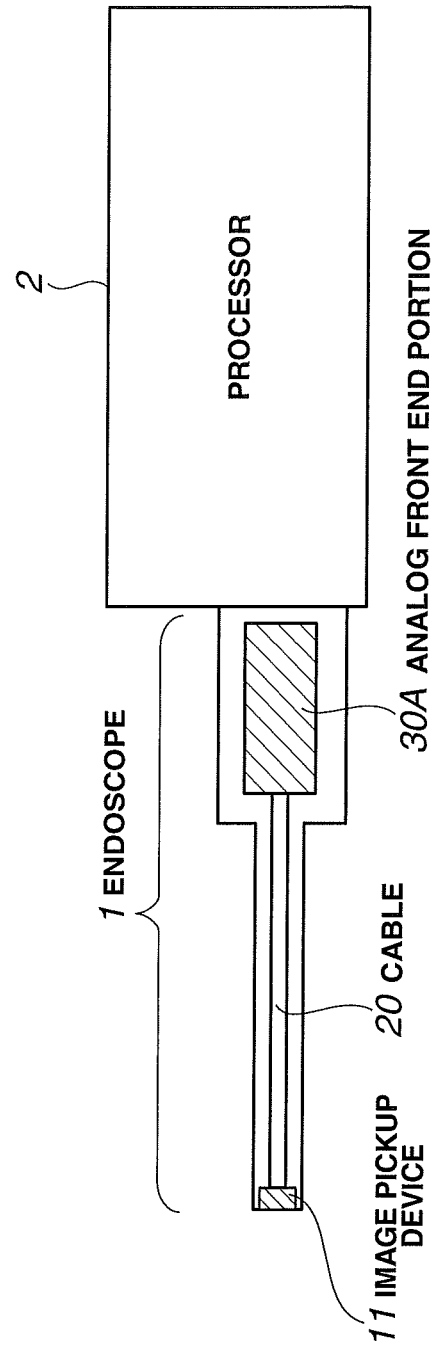
FIG. 6 is a block diagram illustrating Example 1 where an analog front end portion in the impedance matching apparatus according to the first embodiment is installed in an endoscope.

FIG. 6 illustrates a block diagram of Example 1 where an analog front end portion in the impedance matching apparatus of the first embodiment is installed in an endoscope (scope).

In FIG. 6, the analog front end portion 30A smoothes, in the endoscope 1, variations in characteristic impedance of the cable 20 installed in the endoscope 1. Before shipment or in mending (repair), the resistance R4a is adjusted and its result is stored in, for example, ROM in the endoscope 1. On power-up of the endoscope 1, the adjustment result is read out from the ROM to set the resistance R4a.

Figure 7:
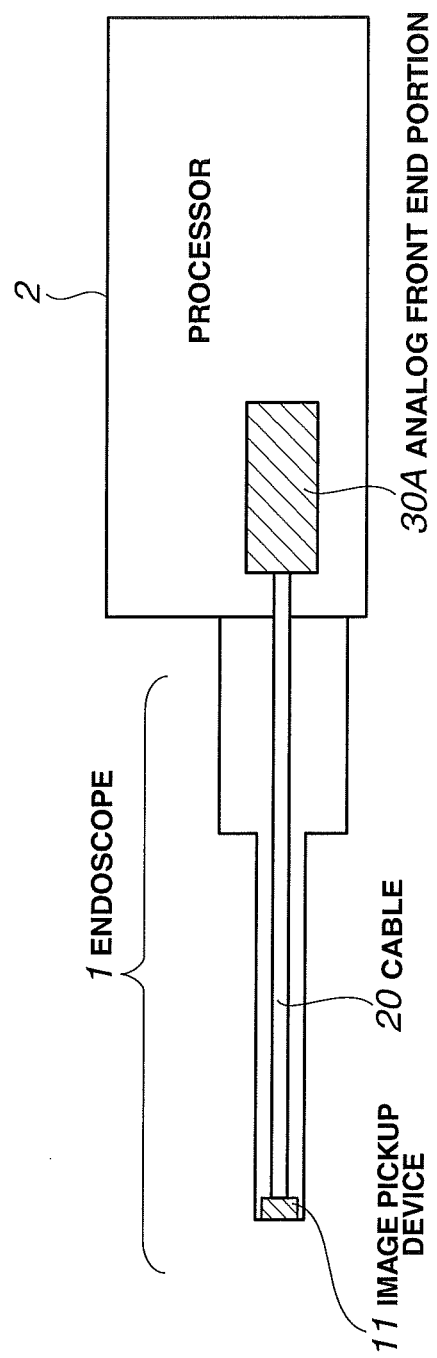
FIG. 7 is a block diagram illustrating Example 2 where the analog front end portion in the impedance matching apparatus according to the first embodiment is installed in a processor.

FIG. 7 illustrates a block diagram of Example 2 where an analog front end portion in the impedance matching apparatus of the first embodiment is installed in a processor.

In FIG. 7, the analog front end portion 30A smoothes, in a processor 2, variations in characteristic impedance of the cable 20 installed in the processor 2. Every time power is applied to the endoscope 1, the resistance R4a is adjusted. The adjustment result is held in a memory in the processor 2 until the power is turned off.

Before this time, inconveniently, an operator has manually adjusted a value of a variable resistance while viewing an observation waveform of CCD output, but according to the first embodiment, it is enabled to provide an impedance matching apparatus that can detect a degree of an impedance mismatch by using sampling of a CDS circuit, which is a correlated double sampling circuit, achieve matching of a resistance value of a variable resistance for matching, and smooth variations in characteristic impedance of a cable used in an endoscope.

[Second Embodiment]

Figure 8:
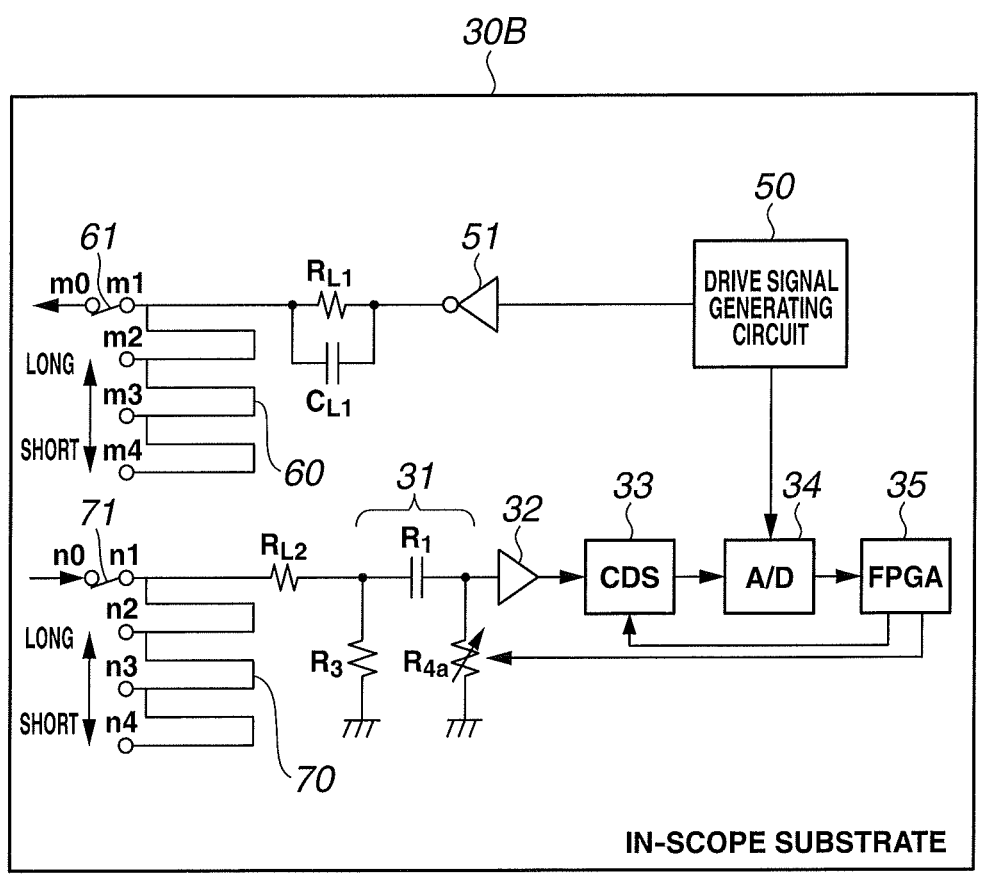
FIG. 8 is a block diagram of an in-scope substrate which can be shared by endoscopes with different cable lengths, in an endoscope including an impedance matching apparatus according to a second embodiment of the present invention.
Figure 9:
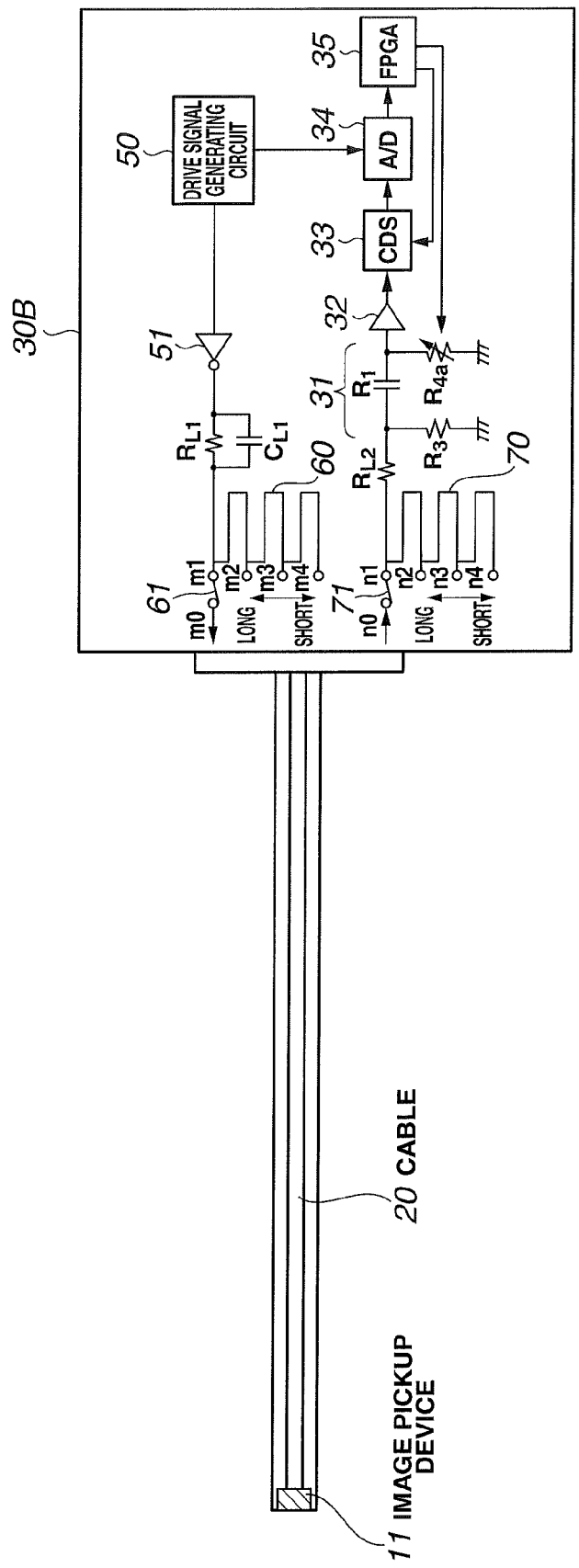
FIG. 9 is a block diagram illustrating a connected endoscope having a long cable in the second embodiment.
Figure 10:
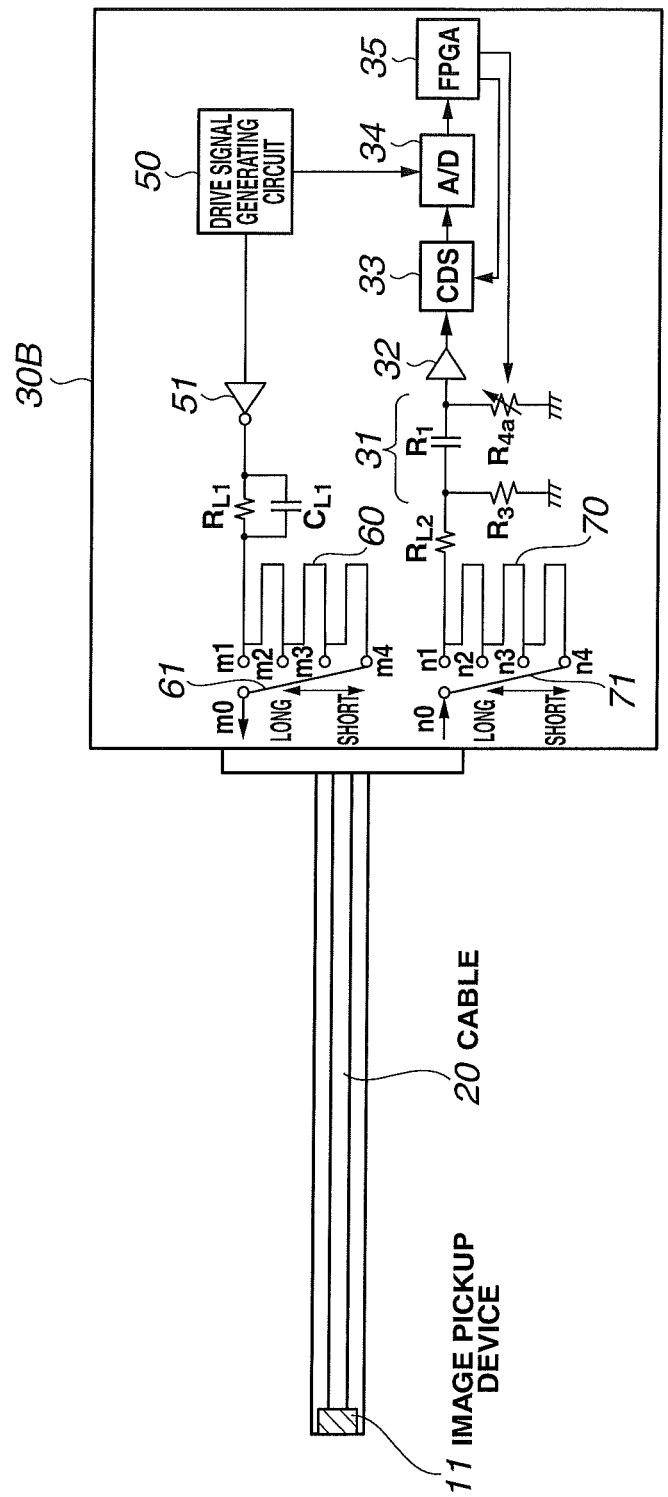
FIG. 10 is a block diagram illustrating a connected endoscope having a short cable, the length of which is compensated, in the second embodiment.

FIG. 8 illustrates a block diagram of an in-scope substrate which can be shared with endoscopes having different cable lengths, in an endoscope including an impedance matching apparatus according to a second embodiment of the present invention. In FIG. 8 to FIG. 10, same reference numerals are assigned to same portions as those in FIG. 1 to denote them.

FIG. 8 illustrates an in-scope substrate 30B that can be incorporated in multiple types of endoscopes in common, having different cable lengths, for example, a long scope such as a colon scope and a short scope such as a bronchial scope.

In the second embodiment, for endoscopes having different cable lengths, signal patterns 60, 70 disposed in the in-scope substrate 30B complement the cable lengths, thereby equalizing a transmission distance between a sending circuit and a receiving circuit of a channel. The signal pattern 60 is a pattern provided on a drive signal line, and the signal pattern 70 is a pattern provided on an image pickup signal line.

Both the signal patterns 60 and 70 are formed into a rectangular wave shape in order to ensure a necessary length in a small space on the substrate. Between a starting end and a tail end of the signal pattern 60, a plurality of (in the figure, four) taps m1 to m4 are provided as electrical connection terminals. A tap m0, which is one common connection terminal, is disposed opposite to the four taps m1 to m4. That is, the tap m0 is enabled to be selectively connected to any one of the taps m1 to m4 using a connection line 61. Thus, the tap m0, the taps m1 to m4, and the connection line 61 compose compensating means that compensates a length of the cable 20 so that the length of the cable 20 becomes substantially a predetermined length.

Similarly, between a starting end and a tail end of the signal pattern 70, a plurality of (in the figure, four) taps n1 to n4 are provided as electrical connection terminals. A tap n0, which is one common connection terminal, is disposed opposite to the four taps n1 to n4. That is, the tap n0 is enabled to be selectively connected to any one of the taps n1 to n4 using a connection line 71. Thus, the tap n0, the taps n1 to n4, and the connection line 71 compose compensating means that compensates a length of the cable 20 so that the length of the cable 20 becomes substantially a predetermined length.

By using the in-scope substrate 30B, which is common in endoscopes, even if the cable 20 having a different length as shown in FIG. 9 or FIG. 10 is connected from outside to the in-scope substrate 30B when an endoscope apparatus is assembled, tap selection in the signal patterns 60, 70 disposed on the in-scope substrate 30B may provide a state equal (equivalent) to a state where a cable having substantially the same length is connected. Thus, only if circuit constants RL1, CL1 and RL2 for phase adjusting and level adjusting in the in-scope substrate 30B are fixed to those corresponding to an endoscope having a longest cable (e.g., a colon scope), in the case where the cable 20 shorter than the longest cable length is connected to the in-scope substrate 30B while the endoscope is being assembled, if appropriate taps (e.g., the taps m4, n4) in the signal patterns 60, 70 are selected from the taps m2 to m4 and the taps n2 to n4 in correspondence with the length of the short cable 20 (e.g., a cable for a bronchial scope) to be actually used, and the selected taps are connected to the common taps m0, n0 using the connection lines 61, 71, then the short cable length is enabled to be matched with the longest one.

If one of the taps m1 to m4 is connected to the common tap m0 sequentially from m1 to m4, as a length of the signal pattern 60 sequentially increases, a cable length added to a drive signal line of the cable 20 externally connected to the tap m0 can be complemented so as to be sequentially lengthened. Similarly, if one of the taps n1 to n4 is connected to the common tap n0 sequentially from n1 to n4, as a length of the signal pattern 70 sequentially increases, a cable length added to an image pickup signal line of the cable 20 externally connected to the tap n0 can be complemented so as to be sequentially lengthened.

Here, it is assumed that impedance matching is unnecessary for the drive signal line, but for the image pickup signal line, if impedance matching apparatuses such as shown in FIG. 1 (reference numerals 31 to 35) are provided, the grade of image pickup signals observed after cable transmission is enabled to be increased.

Conventionally, it has been necessary to design and adjust a circuit constant for each different cable length. Also, since varying cable lengths make transmission time different, disadvantageously, more adjustment has been needed. Namely, conventionally, if cable lengths have been different, phase adjustment prior to A/D conversion has been different for each scope and a circuit constant for driving is needed to be considered for each cable. Thus, an increasing number of scope types have made circuit design and management troublesome.

FIG. 9 illustrates a block diagram of an endoscope with a long cable in accordance with the second embodiment. Here, an endoscope having a longest cable is shown.

In FIG. 9, the connection line 61 is connected between the common tap m0 and the tap m1, and the connection line 71 is connected between the common tap n0 and the tap n1. Namely, the common taps m0, n0 in two switching means in the in-scope substrate 30B are respectively connected to the taps m1, n1 using the connection lines 61, 71. That is, since this is the longest cable connection, length compensation has not been carried out.

FIG. 10 illustrates a block diagram of an endoscope in which a length compensation has been carried out for an endoscope with a short cable length in accordance with the second embodiment. Here, an endoscope having a shortest cable is shown.

In FIG. 10, the connection line 61 is connected between the common tap m0 and tap m4, and the connection line 71 is connected between the common tap n0 and the tap n4. Namely, the common taps m0, n0 in the two switching means in the in-scope substrate 30B are respectively connected to the taps m4, n4 using the connection lines 61, 71. That is, since this is the shortest cable connection, a length corresponding to a full length of the signal patterns 60, 70 has been compensated.

According to the second embodiment, since in an in-scope substrate, the compensating means is provided that compensates a cable length so that the cable length becomes substantially a predetermined length, it is unnecessary to change a circuit constant on the in-scope substrate depending on each cable length and to prepare multiple types of in-scope substrates that depend on cable lengths.

Now, techniques associated with the endoscope according to the present invention will be described below.

Figure 11:
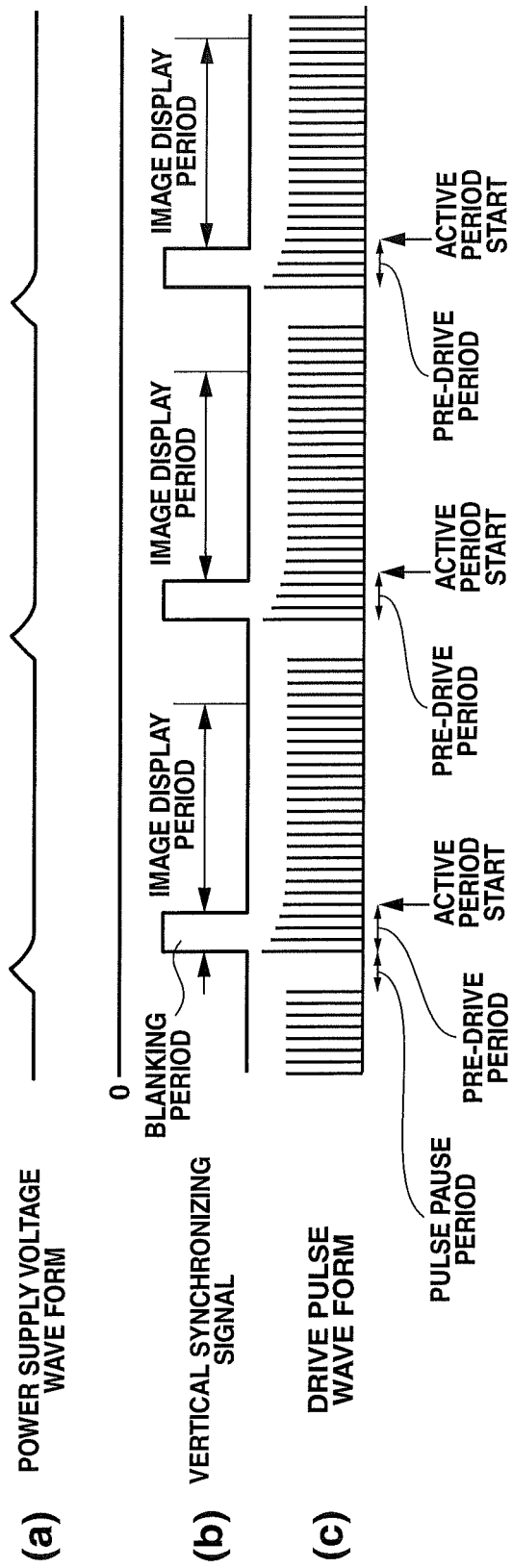
FIG. 11 is a diagram illustrating a method for avoiding an influence of level fluctuations of drive pulses corresponding to changes in a power supply voltage waveform based on drive pulse pause periods.

FIG. 11 illustrates a method for avoiding the influence of fluctuations in levels of drive pulses corresponding to changes in a power supply voltage waveform based on drive pulse pause periods. In FIG. 11, FIG. 11(a) shows a power supply voltage waveform, FIG. 11(b) shows vertical synchronizing signals, and FIG. 11(c) shows a drive pulse waveform. Since drive pulses essentially give drive timing, its amplitude is constant, but in FIG. 11(C), pulse pause periods are provided, so that power supply voltage fluctuates and accordingly drive pulses also fluctuate.

Because as a resolution of a CCD increases, drive signal frequency becomes high and thereby power consumption becomes large. Thus, pause periods are set for drive pulses to save the power consumption. Therefore, the drive pulse has activating periods and stopping periods. At the stopping periods, the power is not consumed, but because the CCD at an endoscope distal end is supplied with power via a cable, when a driving current flows, power supply voltage decreases. If drive pulse is not being activated, since consumption current does not flow, the power supply voltage increases. If drive pulses, which are drive signals, are activated, with the increase of the power supply voltage, amplitude of the drive pulses rises, and with the decrease of the power supply voltage, the amplitude of the drive pulses fall into a steady state. Namely, once the drive pulses are activated and a driving current starts to flow, since a cable has resistance, the power supply voltage falls into a steady state. At the drive pulse pause periods, if the power supply voltage increases, shading (a phenomenon that an image gradually turns into white) occurs in an image pickup image. Conventionally, because drive pulses have been paused in blanking periods of vertical synchronizing signals (high level periods in FIG. 11(b)), disadvantageously, periods at which the power supply voltage is increasing (in the periods, the rise of amplitude occurs at the time of drive pulse starting) have substantially matched with starts of image display periods, thereby leading to a bad influence as such shading.

Thus, as shown in FIG. 11(c), timings of pause periods of drive pulses are set before blanking periods of vertical synchronizing signals; in other words, start timings of the drive pulses are set before start points of image display periods (active periods) (e.g., around starting points of the blanking periods). Namely, pre-drive periods corresponding to amplitude fluctuation periods of drive pulses are brought to the blanking periods, which are the pause periods of image display, and image signals are taken out after a time when the power supply voltage falls and becomes steady and the drive pulse amplitude also becomes steady. Then, the image signals are displayed on a monitor. Thereby, a part corresponding to shading is not displayed on the monitor.

As in FIGS. 11(b) and 11(c) described above, timings for driving are shifted to start prior to actually necessary image display periods and image pickup images are taken after the power supply voltage and the amplitudes of the drive pulses become steady, and thereby a problem such as shading can be prevented from being displayed on the screen.

Figure 12:
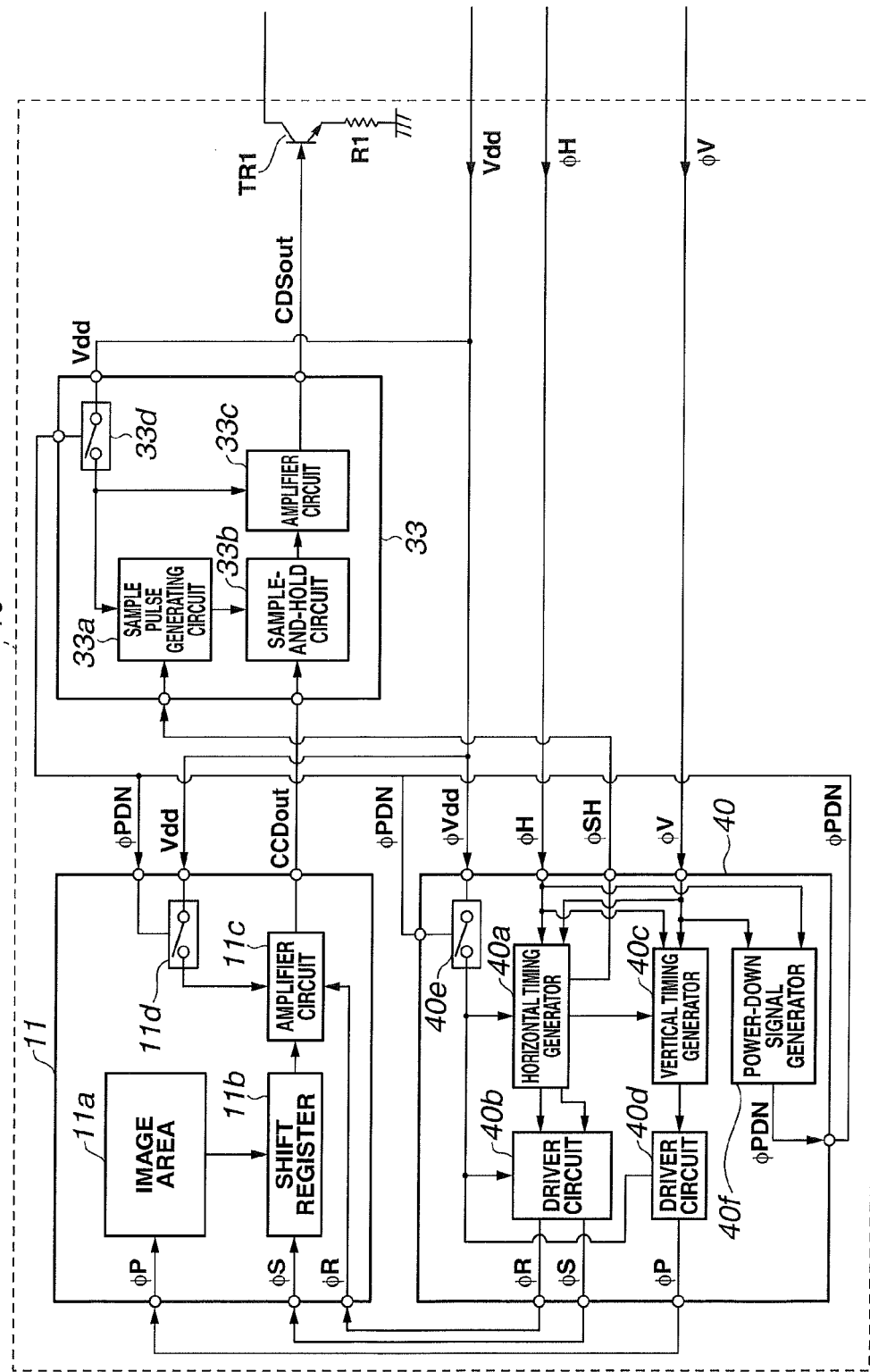
FIG. 12 is a block diagram illustrating a configuration in which a power-down signal generator for pausing read-out pulses within an exposure time in intermittent drive of a frame transfer CCD is disposed in an endoscope distal end portion.

FIG. 12 illustrates a configuration in which a power-down signal generator is disposed at an endoscope distal end portion, the power-down signal generator being used to pause read-out pulses or drive signals for exposure times in intermittent driving of a frame transfer CCD used in an endoscope according to the present invention. It should be noted that the illustrated distal end portion 10 of the endoscope 1 includes the CDS circuit 33 and a timing generator 40, in addition to the CCD 11.

In FIG. 12, the distal end portion 10 of the endoscope 1 includes the CCD 11, the CDS circuit 33 that performs correlated double sampling processing, and the timing generator 40 that supplies these circuits with timing signals. As the CCD 11, for example, a frame transfer scheme CCD is used. Also, the timing generator 40 includes timing generators 40a, 40c and driver circuits 40b, 40d, as well as a power-down signal generator 40f. Conventionally, because a power-down signal generator has been provided not in the endoscope distal end portion 10 but at a processor (not shown), it has been necessary to insert a power-down signal line into the cable 20, and the fact has been a factor of an increased diameter of an endoscope insertion portion. The conventional example is described in FIG. 3 of Japanese Patent Application Laid-Open Publication No. 2009-045366. To overcome the problem, in an example of the present invention, the power-down signal generator 40f is disposed in the endoscope distal end portion 10 and power-down signals are generated at the distal end portion 10 using horizontal drive signals and vertical drive signals.

Now, the circuit configuration shown in FIG. 12 will be described, and then a method for generating a power-down signal will be described with reference to FIG. 13 to FIG. 17.

As shown in FIG. 12, the CCD 11 provided in the distal end portion 10 of the endoscope 1 includes an image area 11a, a shift register 11b, an amplifier circuit 11c, and a switch 11d.

The image area 11a performs photoelectric conversion of an object image formed by an objective optical system, not shown, and accumulates the image as an electric charge, as well as the image area 11a transfers the electric charge to the shift register 11b based on φP signals outputted from the timing generator 40.

The shift register 11b outputs the electric charge transferred from the image area 11a to the amplifier circuit 11c as image pickup signals based on φS signals outputted from the timing generator 40.

If the switch 11d is on, voltage Vdd is supplied, and thereby the amplifier circuit 11c becomes in a driven state. In other words, if the switch 11d is off, since the voltage Vdd is not supplied, the amplifier circuit 11c is in a stopped state. In the driven state, the amplifier circuit 11c amplifies an image pickup signal outputted from the shift register 11b based on φR signals outputted from the timing generator 40, and outputs the amplified image pickup signal to the CDS circuit 33 as a CCDout signal.

If an inputted φPDN signal indicates ON, the switch 11d is turned on to supply the voltage Vdd to the amplifier circuit 11c. Also, if an inputted φPDN signal indicates OFF, the switch 11d is turned off to stop the supply of the voltage Vdd to the amplifier circuit 11c.

As shown in FIG. 12, the CDS circuit 33 provided at the distal end portion 10 of the endoscope 1 includes a sample pulse generating circuit 33a, a sample-and-hold circuit 33b, an amplifier circuit 33c, and a switch 33d.

If the switch 33d is on, voltage Vdd is supplied, and thereby the sample pulse generating circuit 33a becomes in a driven state. In other words, if the switch 33d is off, since the voltage Vdd is not supplied, the sample pulse generating circuit 33a is in a stopped state. In the driven state, based on φSH signals outputted from the timing generator 40, the sample pulse generating circuit 33a generates a sample pulse for indicating a timing at which the sample-and-hold circuit 33b performs correlated double sampling processing, and outputs the sample pulse to the sample-and-hold circuit 33b.

The sample-and-hold circuit 33b performs correlated double sampling processing on CCDout signals outputted from the CCD 11 based on the sample pulse outputted from the sample pulse generating circuit 33a.

If the switch 33d is on, the voltage Vdd is supplied, and thereby the amplifier circuit 33c becomes in a driven state. In other words, if the switch 33d is off, since the voltage Vdd is not supplied, the amplifier circuit 33c is in a stopped state. In the driven state, the amplifier circuit 33c amplifies the CCDout signals on which the correlated double sampling processing has been performed, the signals being outputted from the sample-and-hold circuit 33b, and outputs the amplified CCDout signals to a base of a transistor TR1 as CDSout signals (image pickup signals).

If an inputted φPDN signal indicates ON, the switch 33d is turned on to supply the voltage Vdd to the amplifier circuit 33c. Also, if an inputted φPDN signal indicates OFF, the switch 33d is turned off to stop the supply of the voltage Vdd to the amplifier circuit 33c.

As shown in FIG. 12, the timing generator 40 provided at the distal end portion 10 of the endoscope 1 includes a horizontal timing generator 40a, driver circuits 40b and 40d, a vertical timing generator 40c, and a switch 40e.

If the switch 40e is on, voltage Vdd is supplied, and thereby the horizontal timing generator 40a becomes in a driven state. In other words, if the switch 40e is off, since the voltage Vdd is not supplied, the horizontal timing generator 40a is in a stopped state. In the driven state, the horizontal timing generator 40a generates horizontal timing signals based on inputted φH signals and φV signals, and outputs the horizontal timing signals to the driver circuit 40b and the vertical timing generator 40c. Also, in the driven state, the horizontal timing generator 40a generates φSH signals based on the inputted φH signals and φV signals, and outputs the φSH signals to the sample pulse generating circuit 33a.

If the switch 40e is on, the voltage Vdd is supplied, and thereby the driver circuit 40b becomes in a driven state. In other words, if the switch 40e is off, since the voltage Vdd is not supplied, the driver circuit 40b is in a stopped state. The driver circuit 40b generates and outputs a φS signal that is a signal for driving the shift register 11b based on the horizontal timing signals outputted from the horizontal timing generator 40a, as well as the driver circuit 40b generates and outputs a φR signal that is a signal for driving the amplifier circuit 11c.

The vertical timing generator 40c generates vertical timing signals based on the inputted φH signals, φV signals, and horizontal timing signals, as well as the vertical timing generator 40c outputs the vertical timing signals to the driver circuit 40d.

If the switch 40e is on, the voltage Vdd is supplied, and thereby the driver circuit 40d becomes in a driven state. In other words, if the switch 40e is off, since the voltage Vdd is not supplied, the driver circuit 40d is in a stopped state. The driver circuit 40d generates and outputs a φP signal that is a signal for driving the image area 11a based on the vertical timing signals outputted from the vertical timing generator 40c.

In the case where the driver circuit 40b and the driver circuit 40d are provided at a processor (not shown), if a CCD as a high-resolution image sensor is mounted, drive signals of a high frequency are needed and the high-frequency drive signals are to be transmitted to the CCD 11 in the endoscope distal end portion 10 via the cable 20, but the high-frequency drive signals are attenuated at a high attenuation rate while passing through the cable 20. In contrast, as shown in FIG. 12, if the driver circuits 40b and 40d are provided at the endoscope distal end portion 10, advantageously, the transmission of high-frequency drive signals via the cable 20 is eliminated, and if only horizontal and vertical timing signals are given in the distal end portion 10 part (such signals may be low-level signals of about 1 V), drive signals of approximately 3 V needed for driving are enabled to be generated in the distal end portion 10.

In the above-mentioned frame transfer CCD 11, a transfer path and a photodiode as a photosensitive portion are manufactured mutually, so that trouble is caused by reading charge while light is being received. Thus, in transferring (i.e., reading), light shielding must be provided. Reading time and exposure time must be completely separated from each other. Specifically, reading is carried out while light shielding is provided, and reading cannot be carried out while exposure is performed. Therefore, at an exposure time, even if a read-out signal is received, reading must not be carried out. Namely, it is preferable to disable receiving a read-out signal at an exposure time using a power-down signal. Disabling receiving a read-out signal is also advantageous in that power consumption is saved. Conventionally, light exposure and light shielding with respect to the CCD 11 have been performed using a rotating filter that allows light from a light source apparatus to alternately pass an exposure region and a light-shielding region, so that particularly in a body cavity, because light does not come in from around, the light-shielding region can completely block light, and during the light-shielding period, even if a read-out signal as a drive signal enters the CCD, an image pickup signal can maintain a level of 0. However, it is preferable to completely prevent a read-out signal from entering a CCD because that causes power consumption. Accordingly, in Example 1 of the present invention, at an exposure time, power-down signals denoted by reference character φPDN (at a level L, perform power-down) in FIG. 13 or FIG. 16 are generated to completely stop read-out signals or drive signals.

Figure 13:
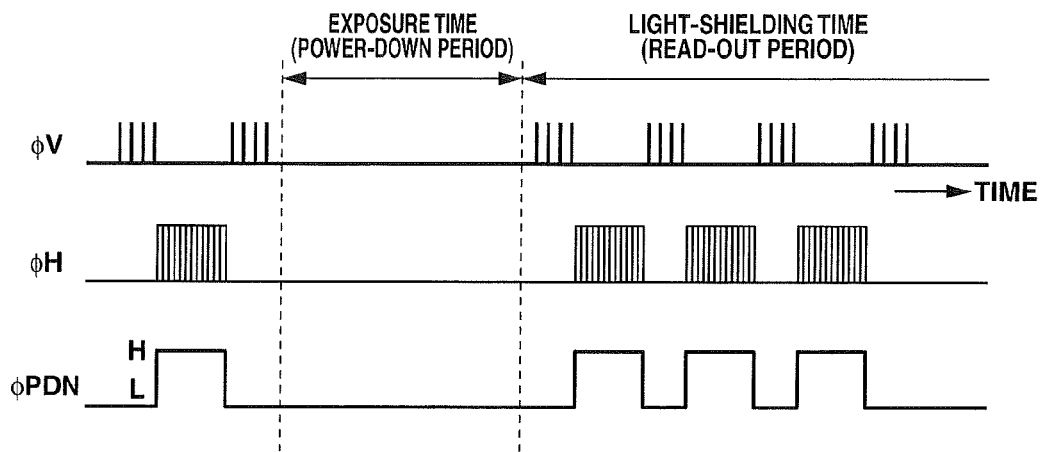
FIG. 13 is a waveform diagram illustrating Example 1 of a power-down signal generating method.
Figure 16:
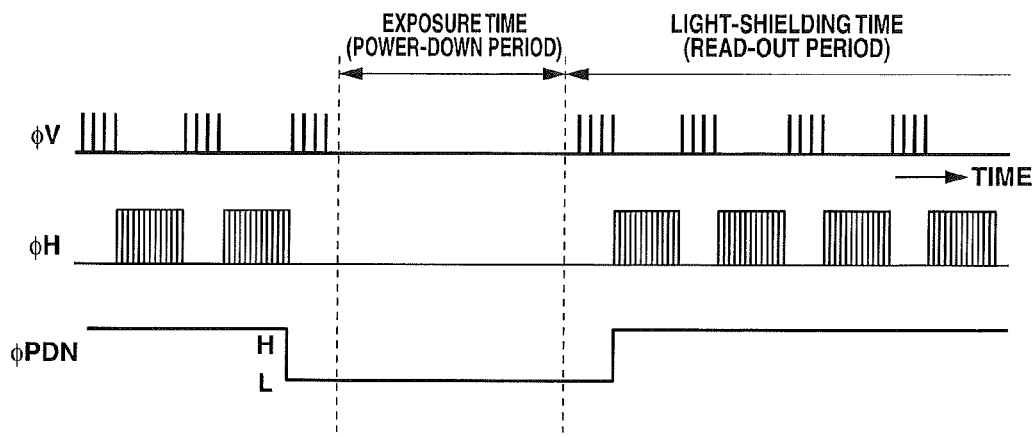
FIG. 16 is a waveform diagram illustrating Example 2 of a power-down signal generating method.

In FIG. 13 and FIG. 16, four lines of signals are shown as vertical read-out signals; it means that four horizontal lines of the CCD are continuously read out and outputted to four horizontal registers (shift registers).

Figure 14:
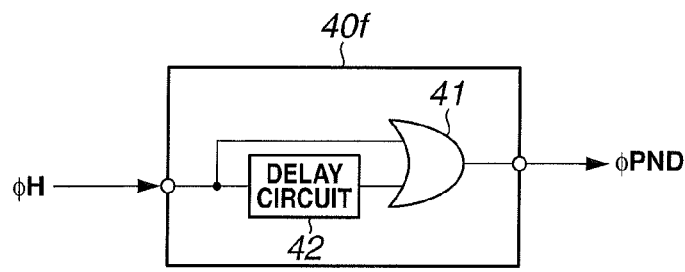
FIG. 14 is a diagram illustrating a configuration of a power-down signal generator in Example 1.
Figure 15:
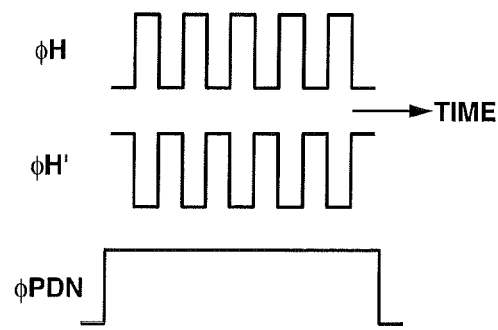
FIG. 15 is a timing diagram illustrating an operation of the power-down signal generator in FIG. 14.

FIG. 13 illustrates Example 1 of a power-down signal generating method, FIG. 14 illustrates a configuration of a power-down signal generator in Example 1, and FIG. 15 illustrates an operation of the power-down signal generator in FIG. 14.

The power-down signal generator 40f shown in FIG. 14 generates φPDN shown in FIG. 13 and includes an OR circuit 41 and a delay circuit 42.

In FIG. 14, by directly inputting horizontal drive signals (e.g., high-frequency signals of 40 MHz) φH to one input end of the OR circuit 41, inputting signals φH' obtained by delaying horizontal drive signals φH for half a cycle to the other input end of the OR circuit 41, and taking a logical sum (OR) of φH and φH', power-down signals φPDN are generated as shown in FIG. 15. When the power-down signals φPDN are at the level L, powering down is performed.

Figure 17:
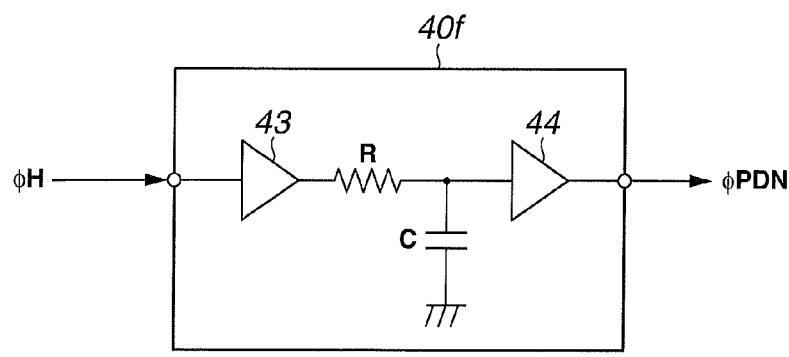
FIG. 17 is a diagram illustrating a configuration of a power-down signal generator in Example 2.
Figure 18:
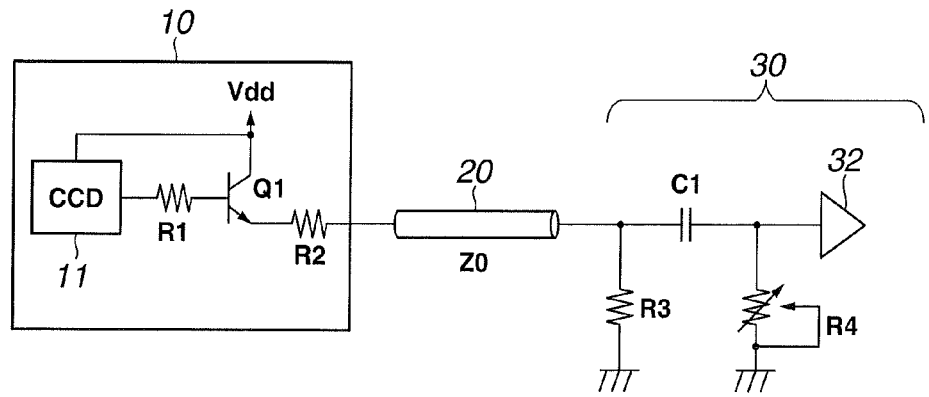
FIG. 18 is a block diagram of an impedance matching apparatus according to a conventional example.
Figure 19:
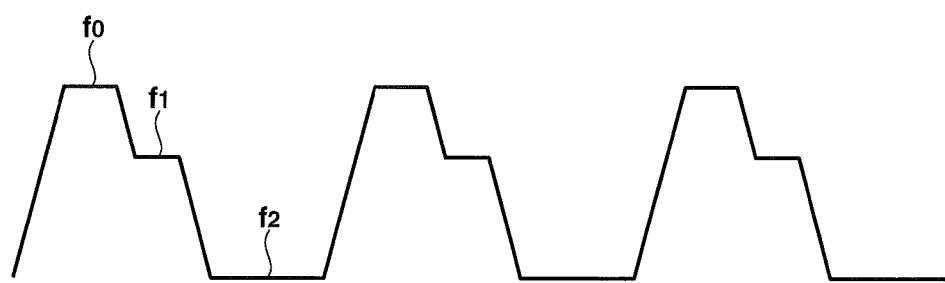
FIG. 19 is a diagram illustrating a CCD output waveform obtained by transmission through a channel with impedance matching being achieved according to the conventional example.
Figure 20:
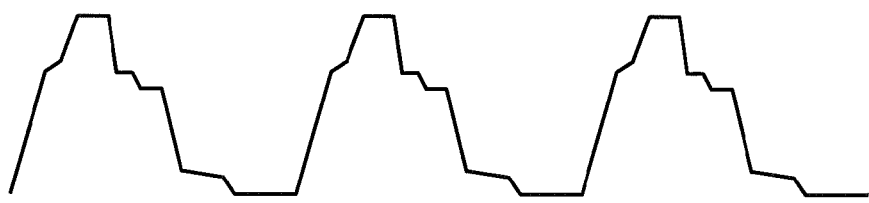
FIG. 20 is a diagram illustrating a CCD output waveform obtained by transmission through a channel with impedance matching not being achieved according to the conventional example.

FIG. 16 explains Example 2 of a power-down signal generating method, and FIG. 17 illustrates a configuration of a power-down signal generator in Example 2.

FIG. 17 illustrates a power-down signal generator that generates power-down signals φPDN as shown in FIG. 16.

In the power-down signal generator 40f shown in FIG. 17, a horizontal drive signal (e.g., a high-frequency signal of 40 MHz) φH is inputted to an integrating circuit of a resistance R and a capacitor C through a buffer amplifier 43, and output of the integrating circuit is outputted as a power-down signal φPDN through a buffer amplifier 44. According to such a configuration, an H level period of the horizontal drive signals φH is held for a certain time period (a substantially horizontal blanking period having no horizontal drive pulses), and thereby power-down signals φPDN with a read-out period having drive pulses as the level H and a power-down period having no drive pulses as the level L, as shown in FIG. 16, can be obtained. Note that in this case, as power-down signals φPDN, signals which do not cause powering-down within a horizontal blanking period are generated.

Because the power-down signals φPDN as shown in FIG. 16 do not cause powering-down within a horizontal blanking period of horizontal drive signals, the effect of power consumption reduction decreases. However, as in the case of the φPDN signals shown in FIG. 13, if powering-down is caused within a horizontal blanking period, at the time of power-on, the operation of a CCD and a CDS circuits is unstable, thereby causing trouble of image quality operation due to waveform distortion or the like. However, according to the power-down signals φPDN shown in FIG. 16, such trouble can be prevented. In the case of the φPDN signals shown in FIG. 13, powering-down is enabled in both the horizontal and the vertical directions, and in contrast, in the case of the power-down signals φPDN shown in FIG. 16, powering-down is enabled only in the vertical direction.

The present invention is not limited to the aforementioned embodiments, and a variety of variations and modifications can be made without departing from the gist of the present invention.

What is claimed is:

1. An impedance matching apparatus comprising:
   a solid image pickup device;
   a driving portion that drives the solid image pickup device so that the solid image pickup device outputs a rectangular wave;
   a cable that transmits the rectangular wave outputted from the solid image pickup device;
   a correlated double sampling circuit that performs correlated double sampling by fixing a timing of a feedthrough sampling pulse to a timing at which the rectangular wave transmitted by the cable indicates a high value, and with the fixed timing of the feedthrough sampling pulse as a basis, sampling the rectangular wave with a timing of a signal clamp pulse being changed to scan the rectangular wave;
   a variable resistance provided at a tail end side of the cable and having a variable resistance value; and
   a resistance value varying portion that based on a signal outputted from the correlated double sampling circuit, changes a resistance value of the variable resistance so that a resistance value of the variable resistance matches a characteristic impedance of the cable.

2. The impedance matching apparatus according to claim 1, wherein the resistance value varying portion differentiates twice a signal outputted from the correlated double sampling circuit, and determines a resistance value of the variable resistance to a resistance value at which an absolute value of a result obtained by the differentiation is a value closest to 0, as a resistance value matching the characteristic impedance of the cable.

3. The impedance matching apparatus according to claim 1, wherein the resistance value varying portion differentiates twice a signal outputted from the correlated double sampling circuit, and determines a resistance value of the variable resistance to a resistance value at which a number of peaks of square values of second derivatives within a predetermined period is a predetermined number, as a resistance value matching the characteristic impedance of the cable.

4. An endoscope including an impedance matching apparatus according to claim 1, wherein the endoscope further comprises compensating means that compensates a length of the cable so that the cable length substantially becomes a predetermined length.

* * * * *